United States Patent
Gutiérrez Pérez et al.

(10) Patent No.: US 9,739,721 B2
(45) Date of Patent: Aug. 22, 2017

(54) APPARATUS FOR INSPECTION OF EXTERNAL CORROSION OF PIPES

(71) Applicant: Corporación Mexicana de Investigación en Materiales, S.A. de C.V., Saltillo (Coahuila) (MX)

(72) Inventors: Jairo Martín Gutiérrez Pérez, Saltillo (MX); Kenia Talía Martínez Arrieta, Ramos Arizpe (MX); Elmer Sanchez Rivero, Saltillo (MX); Juan Antonio Lara Magallanes, Saltillo (MX); Gilberto García Treviño, Saltillo (MX); Jesús Héctor Gerardo García Ortíz, Saltillo (MX); Sergio Vladimiro Marchetti Tiraboschi, Saltillo (MX)

(73) Assignee: Corporación Mexicana de Investigación en Materiales, S.A. de C.V., Saltillo (Coahuila) (MX)

(*) Notice: Subject to any disclaimer, the term of this patent is extended or adjusted under 35 U.S.C. 154(b) by 0 days.

(21) Appl. No.: 15/335,639

(22) Filed: Oct. 27, 2016

(65) Prior Publication Data
US 2017/0131214 A1    May 11, 2017

(30) Foreign Application Priority Data

Nov. 6, 2015    (MX) ................ MX/A/2015/0015392

(51) Int. Cl.
| | | |
|---|---|---|
| *G01N 21/952* | (2006.01) | |
| *F16L 55/00* | (2006.01) | |
| *G01B 11/02* | (2006.01) | |
| *G01N 17/00* | (2006.01) | |
| *G01B 11/06* | (2006.01) | |
| *G01N 17/04* | (2006.01) | |
| *G01N 21/95* | (2006.01) | |

(52) U.S. Cl.
CPC ............ *G01N 21/952* (2013.01); *F16L 55/00* (2013.01); *G01B 11/02* (2013.01); *G01B 11/026* (2013.01); *G01B 11/06* (2013.01); *G01N 17/006* (2013.01); *G01N 17/04* (2013.01); *G01N 2021/9518* (2013.01)

(58) Field of Classification Search
CPC ...... G01N 21/88; G01N 21/952; G01N 17/00; G01N 17/006; G01N 17/04; G01N 2201/06113; G01N 2021/9518; G01B 11/026; G01B 11/06; G01B 11/0608; G01B 11/16; G01B 11/22; G01B 11/24; G01B 11/30; G01B 11/303; G01B 11/306; F16L 55/00
See application file for complete search history.

(56) References Cited

U.S. PATENT DOCUMENTS

| | | | | |
|---|---|---|---|---|
| 4,331,034 A * | 5/1982 | Takeda | ................ | G01N 29/265 376/252 |
| 4,375,165 A * | 3/1983 | de Sterke | ............. | G01N 29/265 73/622 |
| 5,362,962 A * | 11/1994 | Barborak | ................ | E21B 23/00 250/234 |
| 5,370,006 A * | 12/1994 | Zollinger | ........... | G01N 27/9013 324/220 |
| 9,244,024 B1 * | 1/2016 | Patterson | ............... | G01N 23/18 |

(Continued)

*Primary Examiner* — Gordon J Stock, Jr.
(74) *Attorney, Agent, or Firm* — Abelman, Frayne & Schwab (57) ABSTRACT

An apparatus for measuring external corrosion in pipes is disclosed.

9 Claims, 6 Drawing Sheets

(56) References Cited

U.S. PATENT DOCUMENTS

| | | | | |
|---|---|---|---|---|
| 2004/0134289 A1* | 7/2004 | Savard | .................... | F16L 55/38 |
| | | | | 73/865.8 |
| 2009/0307891 A1* | 12/2009 | Offer | .................... | G21C 17/017 |
| | | | | 29/402.11 |
| 2010/0131210 A1* | 5/2010 | Fingerhut | .............. | G01N 27/90 |
| | | | | 702/38 |
| 2011/0167914 A1* | 7/2011 | Sutherland | ................ | F17D 1/00 |
| | | | | 73/643 |
| 2011/0257903 A1* | 10/2011 | Imbert | ................ | G01M 13/045 |
| | | | | 702/35 |
| 2014/0078499 A1* | 3/2014 | Tunheim | ................ | G01N 21/31 |
| | | | | 356/241.1 |
| 2016/0238565 A1* | 8/2016 | Gonzalez | ........... | G01N 29/2487 |

\* cited by examiner

APPARATUS FOR INSPECTION OF EXTERNAL CORROSION OF PIPES

CROSS-REFERENCE TO RELATED APPLICATIONS

This application claims the benefit of priority under 35 U.S.C. 119 to Mexican Patent Application No. MX/a/2015/0015392, filed Nov. 6, 2015, which is hereby incorporated by reference.

TECHNICAL FIELD OF THE INVENTION

The present invention relates to an apparatus for measuring corrosion in pipes. More particularly, the invention relates to an apparatus for measuring external corrosion in pipes through laser with an inspection robot.

BACKGROUND OF THE INVENTION

At present, in the industries, aeronautics, nuclear and oil is being considered as part of its operational policies and security, the preserving the mechanical integrity in their mobile and stationary installations, through actions of maintenance and inspection, which in its most are made with components operating without shutdowns of the plant, especially with regard to inspection.

In the case of the oil industry, through inspection by nondestructive testing is obtained information about the discontinuities and defects in the static components such as pressure vessels and piping in service, information necessary to determine the structural condition of these components and their remaining life time, which helps prevent potential problems and decisions relevant for repairs or maintenance, actions necessary to preserve the structural integrity and therefore the safety of installations.

Particularly in installations of process in the oil offshore platforms there are a lot of pipes, which require periodic inspection to assess their mechanical integrity and increase reliability and security in its functionality, with the particularity that are installed in plants in high seas, in confined spaces at different levels, even "in the air" out of the main structure of the platform, making it difficult inspection, necessitating use at least structures of tubular scaffolding, hanging scaffolding, and ladders, to be in direct contact with the pipes, however the handling and safe installation of these scaffolds turns out to be a process that requires a significant investment of time additional to the activities of inspection of extensions considerably large of pipes, said logistics process includes handling of this tool in plant facilities and installation at every point where there are inaccesible pipes, often it turns out to be a limiting factor for the complete inspection of the plant.

To provide a solution to the limitations mentioned above, Zollinger William T and Treanor Richard C, in the publication of patent application, U.S. Pat. No. 5,370,006A discloses an apparatus for inspecting pipes for use with vehicles to carry out internal inspections surfaces of pipes, which is formed by a front assembly, a back assembly and a central support connected to said assemblies, and an arm for mounting an inspection instrument. This arm has an arm "and" distally mounted for the axial alinement of measuring instrument and a mounting block and a linear actuator for moving the arm to extend the inspection instrument radially out of its position. The apparatus also comprises a rotation motor and gear assembly for rotation of the central support and the front assembly with respect to the rear assembly for inspection through of azimuthal scanning inside the pipe.

Also Barborak Darren M and Bruce William A described in patent publication, U.S. Pat. No. 5,362,962A, a system of measurement of corrosion and a method for measurement and evaluation in significant portions of straight and curved sections of pipes and other surfaces, using an laser instrument with laser light projection through the scan area, which includes corrosion. A positioning mechanism moves the laser instrument along the surface to allow evaluation of the area and a processor controls the operation of both the laser and positioning. An automatic process by the processor converts the surface in an output device.

In view of the foregoing, it is therefore necessary to provide a apparatus of measuring external corrosion of the pipe for an inspection robot, compactly, light weight, small size to allow external inspection of pipes complex arrangements, with obstacles for corrosion, welding or any other irregularity and small thicknesses from four inches in diameter, which allows implement the inspection of corrosion. The present invention can be widely used for maintenance and inspection of pipelines or storage tanks.

SUMMARY OF THE INVENTION

In view of the above described and for the purpose of solving the limitations encountered, it is object of the present invention provide a apparatus measuring of corrosion for pipe inspection robot that has scroll wheels; the measuring apparatus comprises a linear actuator having a stepper motor, a worm driven by the stepper motor and a flange sliding on the worm; a carriage of sensor connected to the flange; a laser sensor located on the carriage of sensor for measuring a thickness of the pipe; a displacement sensor in connection with the stepper motor for sensing an angular displacement of the flange and generating a signal with information of sensing displacement; an angular displacement sensor which is connected to at least one wheel of displacement of robot to sense angular movement of said wheel and generating a signal with information perceived angular displacement; and an mean of processing connected with the sensor of the linear actuator and with the sensor angular displacement of the wheels, wherein the mean of processing receives the signal with information of angular displacement sensing of the linear actuator and the signal with information of displacement angular perceived of wheel to determine coordinates (x, y, z) of movement of said robot on the surface of the pipe.

It is another object of the present invention provide an inspection method of corrosion characterized by comprising the steps of: a) positioning the pipe inspection robot on surface to measuring; b) performing scanning of surface of corrosion of the pipe; c) initiate movement of the linear actuator of apparatus of measuring corrosion; d) measuring the depth of the pipe through laser sensor on the displacement of linear actuator from left to right; e) storing the acquired data of the laser sensor in the processing means; f) repeating steps c, d, e, until the laser sensor traveling along of worm of linear actuator; g) move the wheels of displacement the robot to the desired position; h) measuring the depth of corrosion with the laser sensor on the displacement of the linear actuator from right to left; i) storing the acquired data of the laser sensor in the processing means; j) repeating steps h and i, until the laser sensor traveling along of worm of linear actuator; k) move the wheels of displacement of robot to the desired position; and l) repeating steps until end the surface to scan.

BRIEF DESCRIPTION OF THE FIGURES

The characteristic details of the invention are described in the following paragraphs together with the figures that accompany it, which have to purpose of defining the invention but without limiting its scope.

DETAILED DESCRIPTION OF THE INVENTION

The characteristic details of the invention are described in the following paragraphs, with the purpose of defining the invention but without limiting its scope.

The present invention aims to propose a solution to automate or facilitate the process or activity of inspection and measurement of corrosion of pipes through an apparatus for external inspection with laser, which is compact, lightweight and easy to handle, designed to be positioned in any device mobile that can move on the pipes, which are exposed to an aggressive environment, where layers of paint protection degrade generally or in areas that are affected by corrosion, which produce layers of oxide scale, and for that reason the adhesion strength is lost, and that are outside the scope of the inspector, either by height or position of the platform structure at varying distances up to 8 meters, in different pipe diameters for 4 to 42 inches and can be placed vertically, horizontally and at any point in the circumference of the pipe on the pipe surface to get measurement records and corrosion of wall in steel pipe.

Therefore the present invention relates to a measuring corrosion apparatus for an inspection robot of pipes which has wheels; the measuring device comprises a linear actuator having a stepper motor, a worm driven by the stepper motor and a flange sliding on the worm; a sensor carriage connected to the flange; a laser sensor located on the sensor carriage for measuring a thickness of the pipe; a displacement sensor in connection with the stepping motor for sensing an angular displacement of the flange and generating a signal with linear displacement information received; angular displacement sensor that is connected to at least one of the wheels displacement the robot to sense angular movement of said wheel and generating a signal with information angular displacement received ; and processing means connected with the linear displacement sensor and the angular displacement sensor, wherein the processing means receives the signal with information linear displacement received and the signal with information angular displacement received to determine coordinates (x, y, z) of displacement of said robot on the surface of the pipe.

Figure 1:
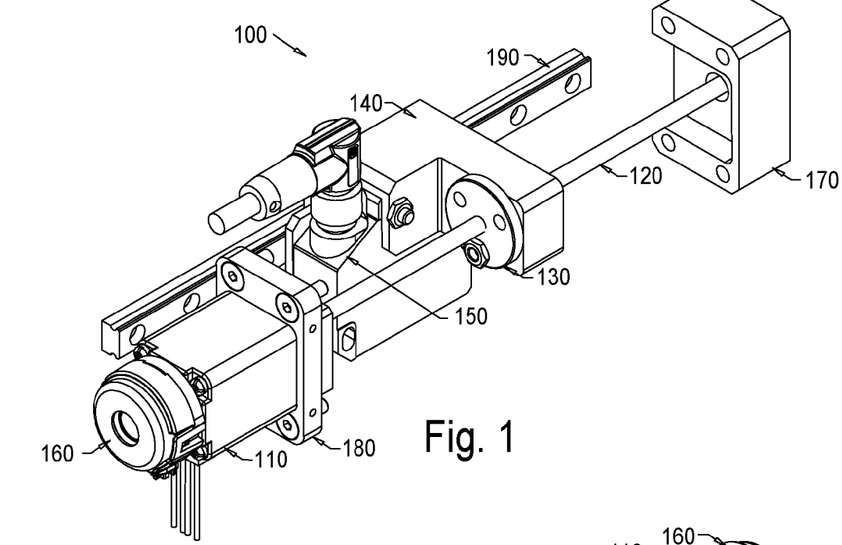
FIG. 1 illustrates an isometric view of an apparatus for measuring external corrosion of pipes according to the invention.

FIG. 1 illustrates an isometric view of a measuring apparatus external corrosion 100 of pipes, which is formed by a linear actuator 110 having a stepper motor (internal), a worm 120 driven by the stepping motor and flange 130 that slides over the screw 120; a sensor carriage 140 connected to the flange 130; a laser sensor 150 located on the carriage sensor 140 for measuring the thickness of the pipe; a sensor of displacement of linear actuator 110 in connection with the stepper motor of linear actuator 110.

The linear actuator 110 is a device composed of a stepping motor with an external actuator integrated to motor of type screw auger (worm) 120 with a linear advance of 8 mm per revolution and a total run of 10 mm; also has counterparty nut, type flange 130 assembled at the base, which serves to support the sensor carriage 140 and displace linearly to the laser sensor 150 throughout his career by a linear guide 190.

The linear actuator 110 has the function to move the sensor 150 along a race or specific straight path to sweep or scan forming a line of points, being a stepper motor, it can also determine the position of the laser sensor according to the steps number advanced by it and with the help of a displacement sensor of linear actuator 110 is verified the accuracy of advance.

The laser sensor 150 is used to measure the distance from a healthy surface to a lower point, ie, the depth of corrosion in the pipe 300, the calibration is performed with reference to healthy surface, and from of that value will be measured the depths of corrosion on the external surface of the pipe 300, the laser sensor 150 is point-like, which moves linearly from right to left and return will be from left to right through the sensor carriage 140 to form a "dotted line" and cover a length of 10 cm corresponding to the length of the actuator stroke, in each of the points a measurement is taken, the sensor provide a voltage output depending on the depth, which is read through an analog pin of control board in charge of processing the signal and convert it in real depth measurement.

The displacement sensor 160 of the linear actuator 110 is a device that transforms and encodes the angular position of a rotating mechanical element, in this case the worm 120 to pulse electronic signal, which is coupled to the stepper motor of linear actuator 110; pulse generating quantified by the control board in each movement. Depending on the displacement of the stepper motor of linear actuator 110, the displacement sensor 160 of the linear actuator 110 generates a number of pulses, which translate into distance, that is, if the screw 120 of the linear actuator 110 moves 8 mm in a revolution and the displacement sensor 160 generates 360 pulses, each pulse is equivalent to a linear advance of 0.02 mm.

The displacement sensor 160 of the linear actuator 110 mechanically interacts with the motor of the linear actuator 110 actuate the displacement sensor 160 with its movement, rotation or spin to generate pulses depending on the angular displacement, also the displacement sensor electronically interacts with the control board, generating through moving the actuator a pulse train. These pulses are counted by the control board via a digital input physically connected to the displacement sensor 160 of the linear actuator 110; the control board interprets or recode these pulses to generate the information on the angular movement of the screw shaft 120 of the actuator 110, which indicates the position or progress of the laser sensor 150 in the X coordinate.

The device measuring external corrosion 100 of pipes, further includes a first mounting base 170 connected to the end of the worm 120 of the linear actuator 110 and a second mounting base 180 secured by screws to the linear actuator 110; where the mounting bases 170 and 180 allow mounting the device measuring corrosion 100 in any robot, vehicle or apparatus wheeled capable of transporting the apparatus measuring corrosion on the surface of the pipe to be inspected.

Figure 2:
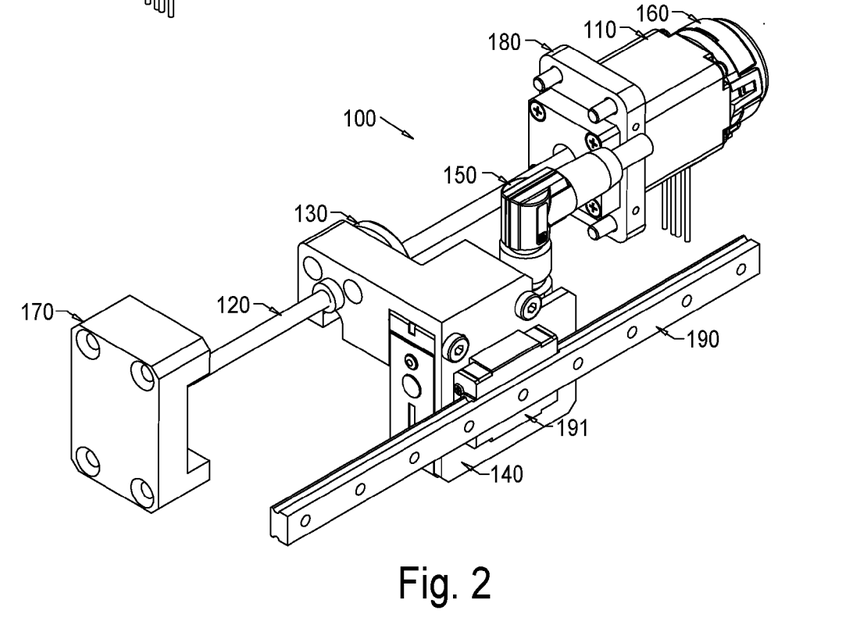
FIG. 2 illustrates an isometric view rear of an apparatus for measurement of external corrosion of pipes according to the invention.

Also the measuring apparatus corrosion 100 further includes a linear slideway 190 attached to the sensor carriage 140 parallel to the worm 120 of the linear actuator 110 by a plate 191 on the back of sensor carriage 140 by screws, the linear slideway 190 has slots allowing sliding sensor carriage 140 during movement of the laser sensor 150 for measuring corrosion; likewise it has perforations that allow attaching it to the robot base or inspection apparatus in question as seen in FIG. 2 is illustrated an back view isometric of a apparatus measurement external corrosion of pipe according to the invention.

The linear slideway 190 is a traslation mechanism which consists of a steel guide that supports the car with internal bearings, this car of guide can support the weight of sensor carriage 140 and the own laser sensor 150, this for prevent the linear actuator 110 holding the weight of both components, and also facilitate the displacement along the worm 120 as it is a component antifriction which no generates resistance to the linear actuator 110 but rather this configuration helps the actuator to move the laser sensor 150 more easily.

Figure 3:
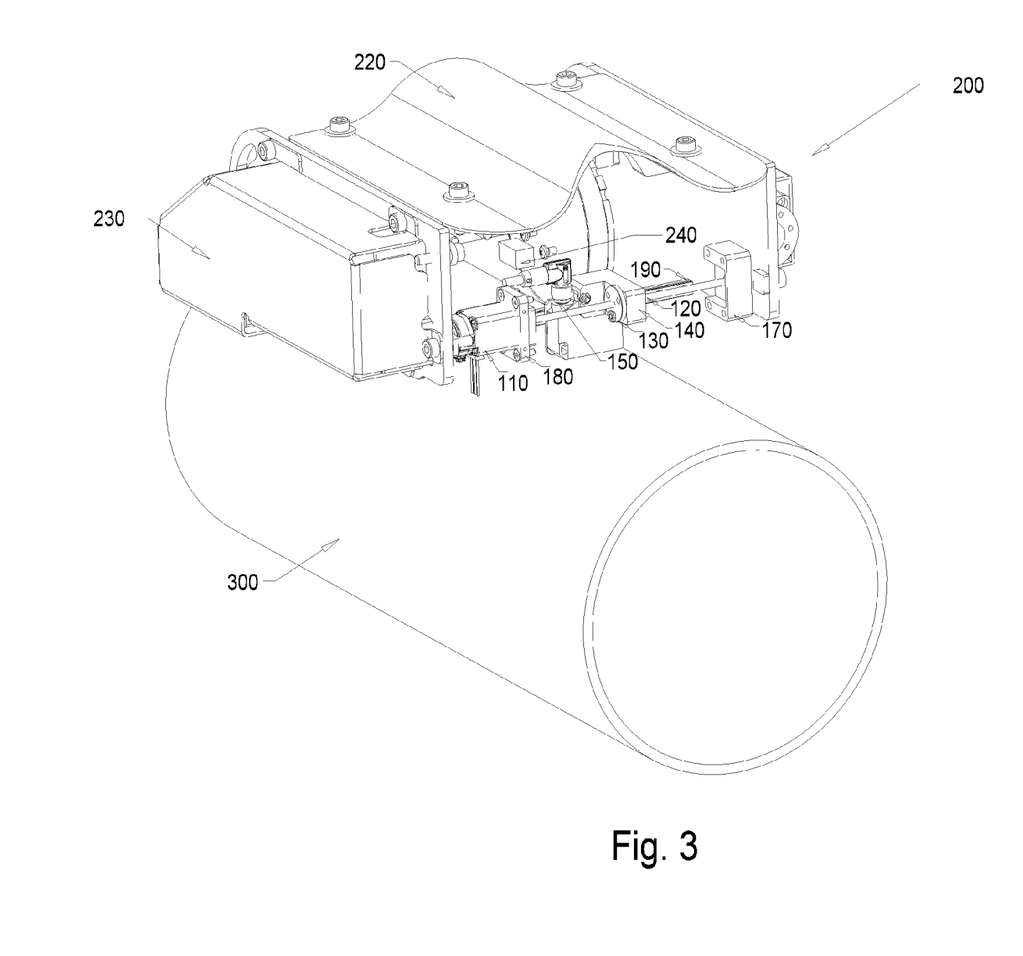
FIG. 3 illustrates a schematic view in perspective of an apparatus for measuring external corrosion of pipes for an inspection robot a first embodiment according to the invention.
Figure 4:
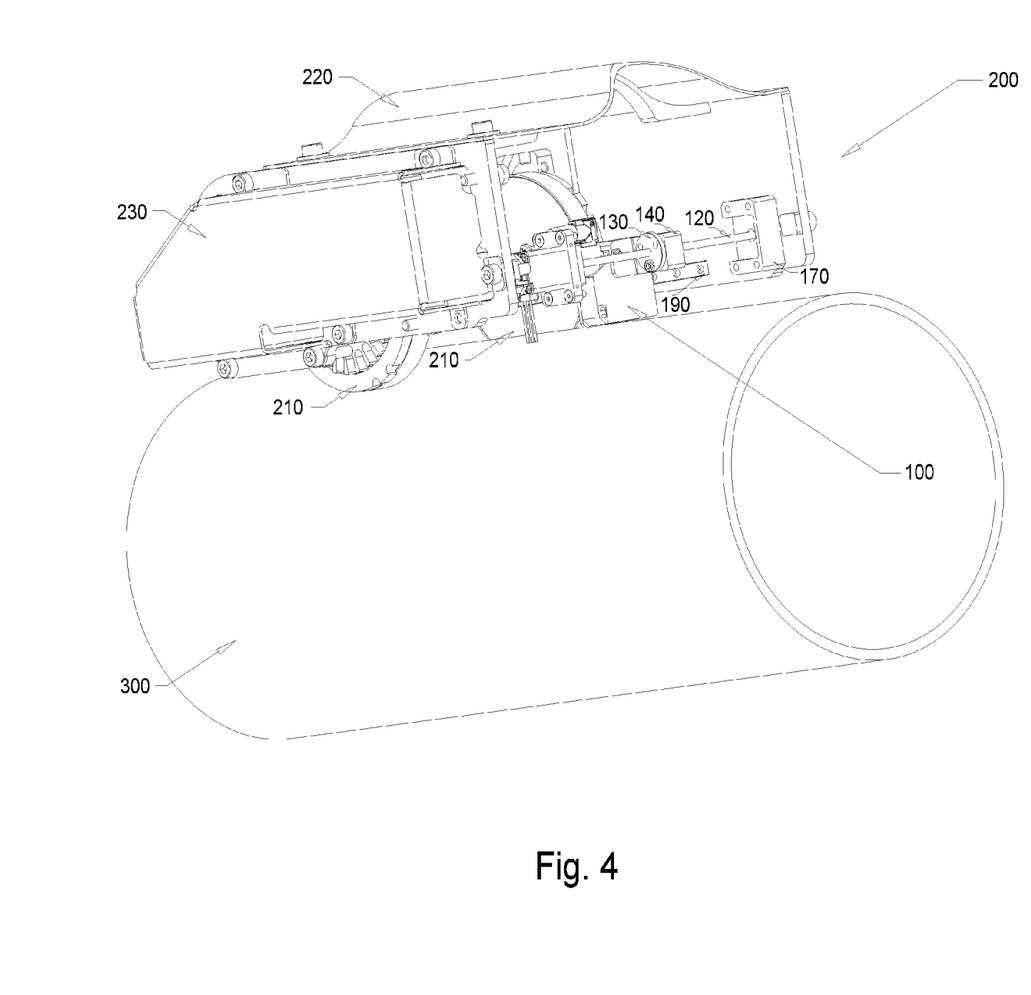
FIG. 4 illustrates a schematic view in perspective of an apparatus for measuring external corrosion of pipes for an inspection robot a first embodiment according to the invention.

In a first embodiment in FIGS. 3 and 4 shown a schematic view in perspective of an apparatus for measuring external corrosion 100 for a robot of inspection 200 of pipes 300 which has a body 220 and with displacement wheels 210 configured to measure the corrosion in pipe surface 300 with longitudinal displacement or displacement on the perimeter of parallel cross sections.

The apparatus 200 for inspection is a whole mechanical system formed by structural parts, mechanical linkages, power transmissions, electrical systems, sensors and control electronics systems, which together with the body 200, the magnetic wheels 210 and the servomotors 230, allow a displacement on the perimeter in transversal sections parallel to the pipe 300, a spiral movement along the pipe 300 and through the longitudinal curvature of the pipe 300.

Figure 5:
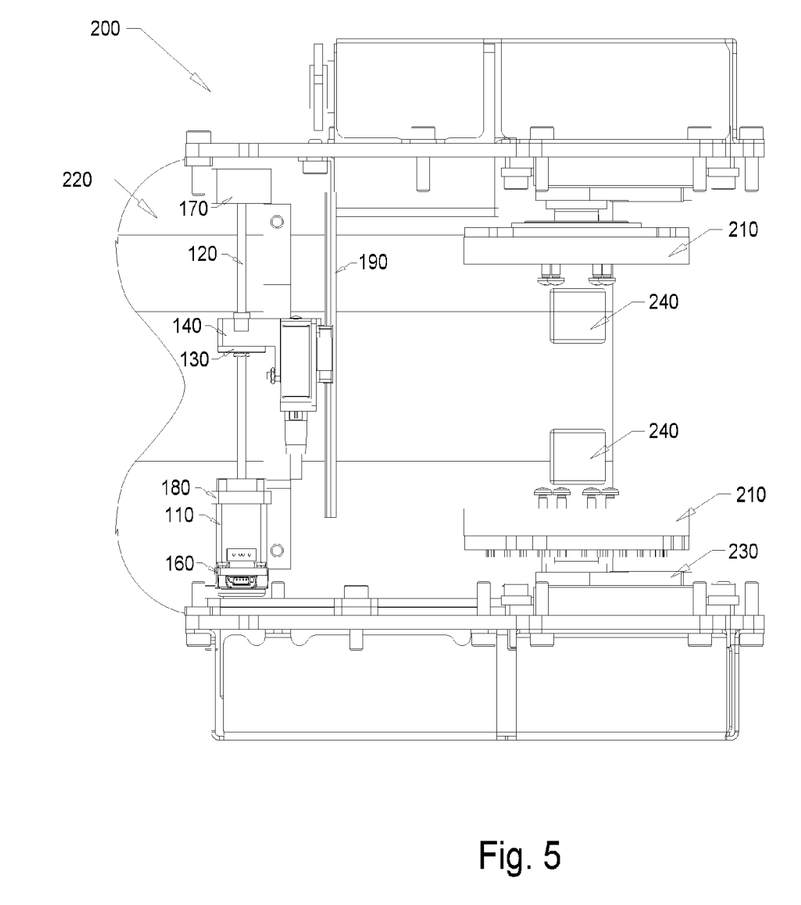
FIG. 5 illustrates a bottom view in perspective of an apparatus for measuring external corrosion of pipes for an inspection robot a first embodiment according to the invention.

In FIG. 5 is illustrated a bottom view in perspective of an apparatus for measuring external corrosion of pipes for an inspection robot in a first embodiment where each of the travel wheels 210 responsible for controlling displacement of the inspection robot 200 are composed of a servomotor 230 allowing movement on the pipe 300 and a sensor of angular displacement 240 connected to perceive the angular movement of the scroll wheel 210 and generate a signal with information angular displacement sensed to determine the coordinate in "y"; this movement will be programmed into the control card of processing means.

The processing means in connection with the displacement sensor 160 of the linear actuator 110 and the displacement sensor 240 of the displacement wheels 210, where the processing means receiving the signal with information perceived of linear displacement and the signal with information of displacement angular perceived to determine coordinates (x, y, z) of displacement of said robot 200 on the surface of the pipe 300.

The displacement sensor 240 of the displacement wheels 210 is a device that transforms and encodes the angular position of a rotating mechanical element, in this case the travel wheels 210 to pulse electronic signal, which is coupled to the servomotor 230 of displacement wheels 210; pulse generating quantified by the card control in every movement. Depending on the displacement of the servomotor 230, the displacement sensor 240 generates a number of pulses which result in distance, that is, if the displacement wheels 210 of the robot 200 moves 8 mm in a turn and the displacement sensor 240 generate 360 pulses, each pulse is equivalent to a linear advancing 0.02 mm.

Moreover the robot 200 has displacement sensors 230 assembled on wheels 210 of the robot 200, a displacement sensor 230 for each wheel 210, each of the displacement sensors 230 are mechanically operated with the movement, rotation, or rotation wheel 210 corresponding to generate pulses in function angular displacement, likewise displacement sensors 230 interact electronically with the control board, generating trough the movement of the wheels 210 a pulse train. These pulses are counted by the control board via a digital input physically connected to the displacement sensor 230; the control board interprets or recodes these pulses to generate the information on the angular movement of each wheel 210 which indicates the advance of the robot 200 in the direction of the coordinate "Y".

The data of advance of the laser sensor 150 in coordinate "X" and advancing of robot in coordinate "Y", in addition to the measurement depth "Z" obtained with the triangulation of laser sensor 150, are sent by the control card through a serial port communication to the processor board, so that it in turn generate the graphical of measurement using software installed on your microprocessor.

The displacement sensor 160 of the linear actuator 110 and the sensor angular displacement 240 is an incremental encoder, and also allow more precise control over displacement wheels 210 and linear actuator 110 also lets you know what the coordinates of the are measurements taken.

The card of motion control based on a microcontroller, which has analog inputs, digital inputs and outputs, serial communication to communicate with the servomotors 230 of the wheels 210 and processing card, which will receive instructions of processing card for controlling the servomotors 230 of the wheels 210 obtaining the forward, reverse and scanning mode, in addition to controlling the linear actuator 110 to move the sensor 150, and converts the voltage signal sent by the laser sensor 150 at a depth in millimeters, thus, processing the signals from the displacement 160 of the linear actuator 110 and the sensor and displacement 240 of the wheels 210 and the laser sensor 150 to form the coordinates, and these data are transferred for storage through a serial port to the processing card; so that it in turn generate the graphical of measurement using software installed on your microprocessor.

The control card is dedicated to control and conversion of pulses and signals to a numerical data obtained through interaction with displacement sensors 240 of the two wheels 210, the displacement sensor 160 of the linear actuator 110 and the laser sensor 150.

The processing card is a minicomputer with a microprocessor with inputs and outputs, which offer the graphical environment to control the movement of the wheels 210 of the robot 200 through a tablet/pc, using a graphical interface where is sent the order of movement to servomotors 230 and is responsible for storing removable media all information collected from the scans, in addition to graphically show the topography of the scanned corrosion.

The processing card interacts with the motion control card sending commands via the serial port such as speed required to motor or determine the start time of the scan. The processing card communicates with a mobile device wirelessly through a network, which shows in a graphical environment with motion controls and scan, plus the results obtained in 3D graphics.

Figure 6:
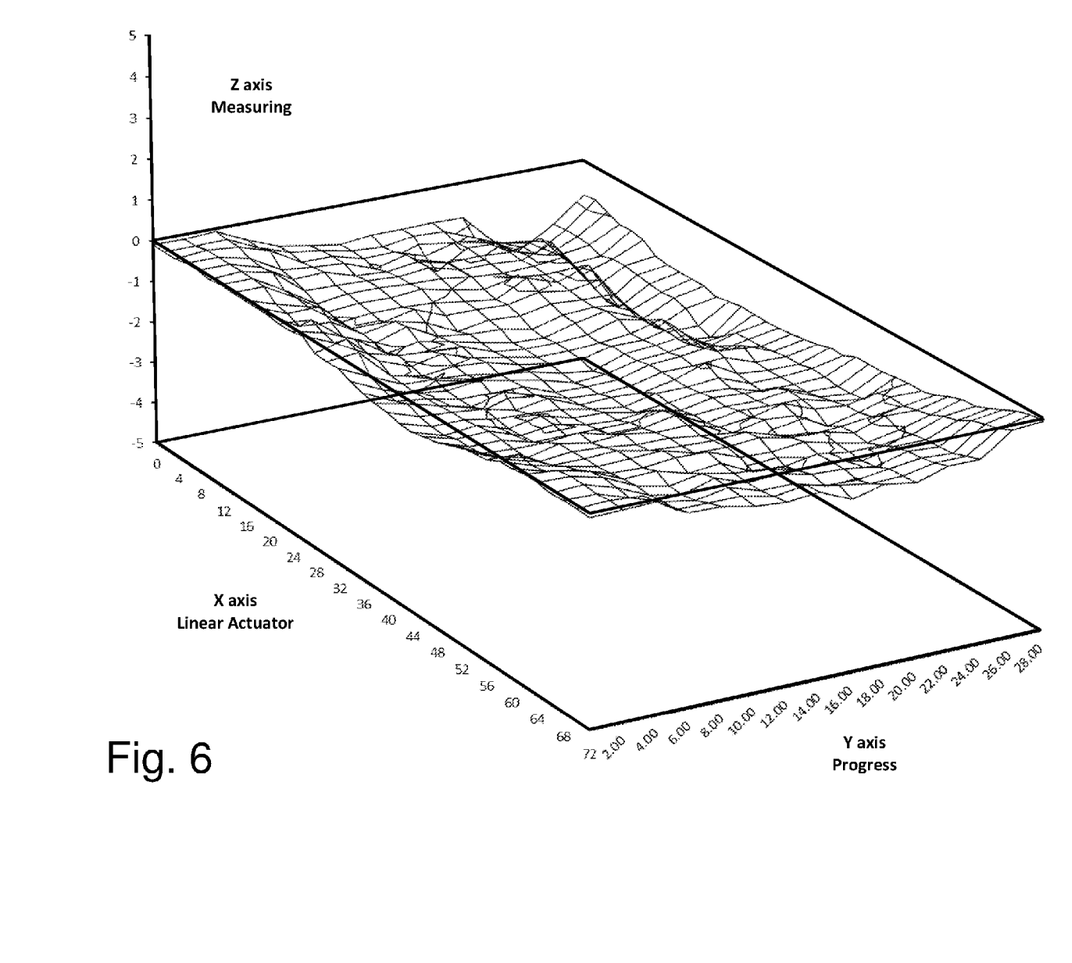
FIG. 6 illustrates a graph in 3d, representative of external corrosion of the surface of a pipe according to the invention.

In FIG. 6 shown a chart representative of surface corrosion in a pipeline; developed where is observed the surface condition, and the position data to a specimen of runs, as described above the measuring device 100 for an inspection robot 200 is moved along the surface to obtain data for assessing the surface of the pipe 300; an example of the data produced by the coordinates (X, Y and Z) are represented in three dimensions, the measured points are approximately 2500 to an area of 10 cm×10 cm intervals 2 mm, which are processed by the processing card represented trough a topographical map, where you can see the different depths, where the analyzed surface has a thickness of 5 mm for a pipe 2 inches in diameter. The device acquires coordinates during the measurement process, and graphics, obtained a topography about corrosion, which is an advantage over the traditional method that use manual tools, because a much larger number of data are obtained quickly and accurately; on data obtained from this scan, was obtained a maximum depth of 2.03 mm located at the coordinates X=21.14, Y=17.

The laser sensor 150 is a device that measures distance by triangulation at a single point, to obtain a topography of corrosion spots, a mesh of points is performed with samples taken from the surface of the pipe, these points are used for reconstruction of surface in precise coordinates in addition to the precise depth measurement, based on the coordinates (X, Y, Z).

The laser sensor 150 performs measurement about inspection area by triangulation at a single point, to obtain topography of corrosion spots, a mesh of points will be made from samples taken from the surface of the pipe, and these points are used to reconstructing the surface in precise coordinates, additional of the accurate depth measurement.

To achieve this requires three coordinates of which are; X: is the distance at which the linear actuator 150 moves to laser sensor in one sweep; Y: It's the distance the same robot moves forward after each sweep and Z: is the measurement of the surface itself, ie, depth from a reference or healthy surface. Graphed these three coordinates, is obtained representation in 3D of a patch of corrosion including the depth of each point and the total length of the stain.

Figure 7:
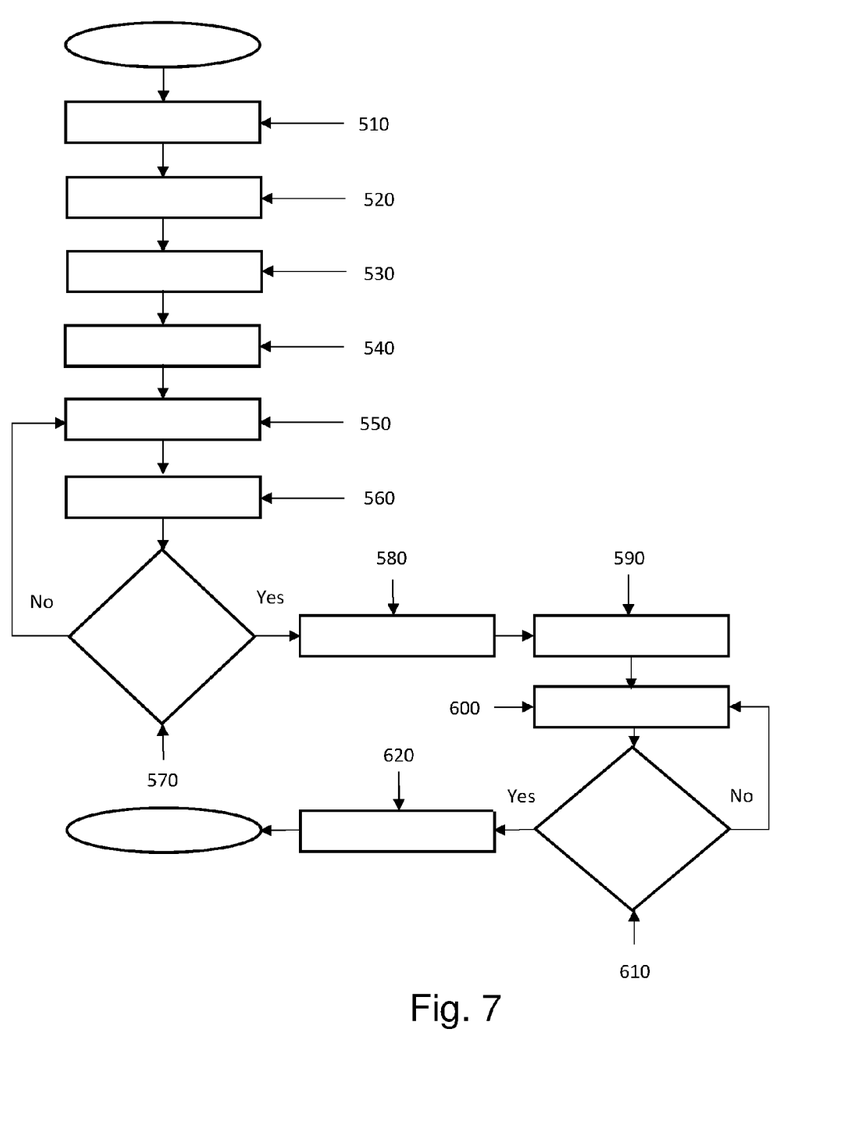
FIG. 7 illustrates a schematic view of the method of measuring of external corrosion of the surface of a pipeline according to the invention.

The measurement method of the apparatus of measuring corrosion 100 is illustrated in FIG. 7, which is a system of close loop control, ie there is a feedback from sensors angular displacement 240 installed on the displacement wheels 210 and the displacement sensor 160 on the linear actuator 110, to determine the precise movements about apparatus of measuring corrosion 100.

The processing means are formed by a processing card and control card; to initiate movement of the linear actuator 110 in first step 510, the processing card instructed to the control board, start scanning; in step 520 the control board is instructed to start scanning and initializes the variables of position of sensor angular displacement 240 and of movement of the motor 230 of displacement wheels 210 and initializes the position variables of displacement sensor 160 the linear actuator 110 and of motor movement of linear actuator 110 to "0" where the current position in the pipe 300 is the reference source for the coordinates to be obtained.

In step 530 once initialized the position variables in "0", the control card generates pulses at a certain frequency, each pulse represents the movement of a step for motor of linear actuator 110, with this starts the movement of linear actuator 110 continuously; Meanwhile in step 540 the displacement sensor 160 of the linear actuator 110 produces pulses when the linear actuator 110 is moved, which are counted by the control board, so acquired a ratio of pulses per revolution of 360 pulses of displacement sensor of linear actuator 110 which is equivalent to 1 turn of the linear actuator 110 and equivalent to 8 mm of advance linear of sensor carriage 140 on worm 120.

Subsequently in step 550 the control card calculates the advance of the linear actuator 110 where each 360 pulses of displacement sensor of the linear actuator 110 of the linear actuator 110 equals 8 mm linear advance; Therefore 90 pulses is equivalent to 2 mm linear advance of movement of sensor carriage 140 on the worm 120 of the linear actuator 110 where the control board takes the data of each point with the laser sensor 150; when the laser sensor 150 is at the point of measurement indicated each 2 mm, the control board, measures the analog signal coming from the laser sensor 150, the signal covers a range of 0V to 3.3V which represents a measurement of 16 mm 120 mm deep.

Then in step 560 the control card keep the data acquired by the laser sensor 150 and processes it as a coordinate three-dimensional (x, y, z) where "X" is the coordinate acquired by the displacement sensor 160 of linear actuator 110 and "Y" is the coordinate acquired by the angular displacement sensor 240 of the wheels 210 and "Z" is the measurement of the laser sensor 150 of all coordinates in millimeters. In step 570 the process is repeated until the sensor carriage 140 with the laser sensor 150 reaches the end of the worm 120 of the linear actuator 110, when it detects that a sweep of points already was performed, the sensor carriage 140 with the laser sensor 150 stops at the end point and is continued to move the wheels 210 of the robot 200.

In step 580, the engines 230 of displacement wheels 210 are still in the position "0", the control board drives the motors 230 forward at the same rate; the angular displacement sensor 240 in each of the wheels 210, produces pulses when the wheels 210 rotate about its axis, which are counted by the control card. The control board counts the pulses of the angular displacement sensors 240 of the wheels 210, and a relationship is obtained; the angular displacement sensor 240 produces 1000 pulses per revolution of the wheel 210, the wheel 210 advances 18 cm lap.

In step 590 the control board calculates when have a displacement of 2 mm with two wheels 210 and when this condition is met, control board stops the motors 230 of the wheels 210, the robot 200 has advanced 2 mm and the laser sensor 150 is located at the end point of the worm 120. In step 600 the control board generates pulses again so that the sensor carriage 140 with the laser sensor 150 returns to its initial position; the control board detects decrements 90 pulses with the signal of the displacement sensor 160 of the linear actuator 110 and in each decrement, the sensor laser performs the measurement as in step 550, each that the point measurement is taken, the card control keep this coordinate (x, y, z) as in step 570, but this time, the coordinate "Y" has increased 2 mm then was made an advance of robot 200 forward.

When the sensor carriage 140 returns to its initial position, in step 610 the control board stops the movement of the linear actuator 110, and is preparing to move the device forward again as in step 600, now the coordinate "Y", increases again 2 mm. The procedure is repeated until end of corrosion zone of the pipe 300.

Finally in step 620 the control card sends all coordinates stored to processing card, which receives and stores and processes all coordinates and creates an array with all measurements, calculates the length of corrosion and gets the point greater depth and proceed to perform 3D graphics.

The apparatus of measuring external corrosion of pipes is remote handling, its compact and lightweight, designed to position it on the pipe 300 that is outside the scope of the inspector through the inspection robot 200, either the height or position of the platform structure, at varying distances up to 8 meters in different pipe diameters and which can be placed anywhere in the pipe for get at least 4 readings of wall thickness steel pipe carbon mainly.

Through inspection activities carried out with the corrosion measuring device 100 for inspection of pipes 300, you can get readings thickness of the pipe wall as well as pictures of surface defects and faults respectively; It is how will the basic information to determine the conditions of corrosion of these components in order to determine its current structural state and make decisions concerning the maintenance of each circuit inspected section or entire sections of pipe in service. With this inspection apparatus can be reviewed pipes ranging from 4-42 inches in diameter of ferromagnetic material.

The operation of the apparatus for measuring corrosion 100 and the robot 200 are remotely controlled remotely by the control unit and inspection processing, which is basically responsible for manipulating the movement and stability of the apparatus 200 to be located in the point of the pipe 300 to be analyzed, via a wireless telecommunication system in real time and thus it has the function of gathering and processing data during the analysis through the transducer via microdot cable and visual monitoring system, which are sent to the receiver monitor for further processing and analysis, this through cable of interconnecting.

The maximum dimensions of the measuring apparatus external corrosion 100 are 17.1 cm long, 49.96 cm wide and 51.51 cm in height. In addition, the material that is made is aluminum, which allows suits to environmental conditions of high salinity, humidity up to 90% allowing a simple way to carry out activities of non-destructive testing pipeline in service; specifically pipe installed in inaccessible spaces, heights and confined spaces.

It should finally be understood that the apparatus measuring corrosion of pipe with laser, according to the invention are not limited to the embodiment or embodiments described above and that those skilled in the art will be trained by the teachings set forth herein, to make changes in the composition of the inspection apparatus of the present invention, the scope of the invention will be established only by the following claims:

We claim:

1. An apparatus measuring corrosion for a robot inspection of pipe which has displacement wheels; the apparatus comprising:
    a linear actuator having a stepper motor, a worm driven by the stepper motor and a flange sliding on the worm;
    a sensor carriage connected to the flange;
    a laser sensor located on the sensor carriage for measuring a thickness of the pipe;
    a displacement sensor of linear actuator in connection with the stepping motor for sensing an angular displacement of the flange and generating a signal with information about perceived linear displacement;
    an angular displacement sensor connected to at least one of the displacement wheels of the robot for sensing angular movement of said wheel and generating a signal with information about perceived angular displacement; and
    processing means connected with the displacement sensor of the linear actuator and sensor angular displacement, wherein the processing means receives the signal with information angular displacement sensed of the linear actuator and the signal with information of the angular displacement perceived of wheels to determine coordinates (x, y, z) of movement of said robot on the surface of the pipe.

2. The apparatus for inspection of claim 1, including a linear slideway attached to said sensor carriage in parallel to said worm.

3. The apparatus for inspection of claim 1, including a mounting base located at the end of the worm of linear actuator.

4. The apparatus for inspection of claim 1, including a mounting base located in the linear actuator.

5. The apparatus for inspection of claim 1, wherein the apparatus is mountable and removable from any pipeline inspection apparatus.

6. The apparatus for inspection of claim 1, wherein operation of said inspection apparatus is remotely controlled.

7. The apparatus for inspection of claim 1, wherein the laser sensor will get spot measurement on the surface of the pipe.

8. The apparatus for inspection of claim 1, wherein the processing means are formed by a control card and a processing card.

9. An inspection method of corrosion of pipe, utilizing the apparatus for inspection of claim 1, and comprising the steps of:
    a) positioning the pipe inspection robot on surface to be measured;
    b) performing scanning on surface of corrosion of the pipe;
    c) initiating movement of the linear actuator of corrosion measuring apparatus;
    d) measuring the depth of the pipe with laser sensor on the displacement the linear actuator from left to right;
    e) storing the acquired data of the laser sensor in the processing means;
    f) repeating steps c, d, e, until the laser sensor travel end through the worm of linear actuator;
    g) moving the displacement wheels of the robot to the desired position;
    h) measuring the depth of corrosion with the laser sensor on the displacement of the linear actuator from right to left;
    i) storing the acquired data of the laser sensor in the processing means;
    j) repeating steps h and i, until the laser sensor travel end through the worm of linear actuator;
    k) moving the displacement wheels of the robot to the desired position; and
    l) repeating steps until end the scan surface.

* * * * *